(12) United States Patent
Owen

(10) Patent No.: US 9,132,116 B2
(45) Date of Patent: Sep. 15, 2015

(54) MAST CELL STABILIZERS TO PREVENT OR TREAT LAMINITIS

(75) Inventor: Charles F. Owen, Littleton, CO (US)

(73) Assignee: WILLOWCROFT PHARM INC., Denver, CO (US)

( * ) Notice: Subject to any disclaimer, the term of this patent is extended or adjusted under 35 U.S.C. 154(b) by 341 days.

(21) Appl. No.: 12/510,750

(22) Filed: Jul. 28, 2009

(65) Prior Publication Data

US 2009/0304648 A1 Dec. 10, 2009

Related U.S. Application Data

(63) Continuation-in-part of application No. 12/387,166, filed on Apr. 29, 2009, now abandoned, which is a continuation-in-part of application No. 11/047,068, filed on Jan. 31, 2005, now abandoned.

(60) Provisional application No. 60/598,186, filed on Aug. 2, 2004.

(51) Int. Cl.
*A61K 31/352* (2006.01)
*A61K 31/436* (2006.01)
*A61K 31/519* (2006.01)

(52) U.S. Cl.
CPC ............. *A61K 31/352* (2013.01); *A61K 31/436* (2013.01); *A61K 31/519* (2013.01)

(58) Field of Classification Search
CPC .................................................. A61K 31/352
See application file for complete search history.

(56) References Cited

U.S. PATENT DOCUMENTS

| | | | | |
|---|---|---|---|---|
| 4,192,860 | A * | 3/1980 | Griffiths | 424/43 |
| 4,234,566 | A * | 11/1980 | Packman et al. | 424/47 |
| 4,419,352 | A | 12/1983 | Cox et al. | |
| 4,897,268 | A | 1/1990 | Tice et al. | |
| 4,918,078 | A | 4/1990 | Brown et al. | |
| 5,075,109 | A | 12/1991 | Tice et al. | |
| 5,256,680 | A * | 10/1993 | Connor et al. | 514/364 |
| 5,811,094 | A * | 9/1998 | Caplan et al. | 424/93.7 |
| 6,080,748 | A * | 6/2000 | Uckun et al. | 424/178.1 |
| 6,534,526 | B2 | 3/2003 | Cross | |
| 2006/0173071 | A1 | 8/2006 | Owen | |

FOREIGN PATENT DOCUMENTS

| | | |
|---|---|---|
| GB | 2022078 | 6/1978 |
| WO | WO 2008/034740 A1 | 3/2008 |

OTHER PUBLICATIONS

Carroll J. "Stem cells and HD: past, present and future" www.HDBuzz.com. 2011.*
Garner MR, Flint JF, Russell JB. Allisonella histaminiformans gen. nov., sp. nov. A novel bacterium that produces histamine, utilizes histidine as its sole energy source, and could play a role in bovine and equine laminitis. Syst Appl Microbiol. Dec. 2002;25(4):498-506.*
Huang ZL, Mochizuki T, Watanabe H, Maeyama K. Histamine release induced by immobilization, gentle handling and decapitation from mast cells and its inhibition by nedocromil in rats. Jpn J Pharmacol. Jul. 1999;80(3):255-62.*
The Ultimate Horse Site. "Founder" http://www.ultimatehorsesite.com/info/founder.html Dec. 2004 (from archive.org: http://web.archive.org/web/20041213220057/http://www.ultimatehorsesite.com/info/founder.html) accessed Aug. 26, 2011.*
Bergsten C. Laminitis: Causes, Risk Factors, and Prevention, 2011.*
Pearce FL, Al-Laith M, Bosman L, Brostoff J, Cunniffe TM, Flint KC, Hudspith BN, Jaffar ZH, Johnson NM, Kassessinoff TA, et al. Effects of sodium cromoglycate and nedocromil sodium on histamine secretion from mast cells from various locations. Drugs. 1989;37 Suppl 1:37-43 (abstract only).*
American Blacksmith, 2001. https://web.archive.org/web/20011224123846/http://www.americanblacksmith.com/blacksmithstable/laminitis_&_founder.htm.*
University of Pennsylvania, 2001. http://cal.vet.upenn.edu/projects/fieldservice/Dairy/LAMENESS/laminits.htm.*
Alexander (2013) "The Concise Guide to Pharmacology, G Protein-Coupled Receptors," Br. J. Pharmacol. 170:1459-1581.
International Search Report and Written Opinion, PCT/US2009/051947, mailed Sep. 23, 2009, 6 pages.
Proceedings of the 11th International Congress of the World Equine Veterinary Association, Sep. 24-27, 2009, Guarujá, SP, Brazil.
White "Equine Laminitis" Marion duPont Scott Equine Medical Center VA-MD Regional College of Veterinary Medicine Virginia Tech, Leesburg, VA 22075.

* cited by examiner

*Primary Examiner* — Paul Zarek
(74) *Attorney, Agent, or Firm* — Brownstein Hyatt Farber Schreck, LLP; Paul J. Prendergast

(57) ABSTRACT

Provided herein are mast cell stabilizers used to prevent, treat, or mitigate severity of laminitis. Mast cell stabilizers can be combined with antihistamines and other medicaments to prevent, treat, or mitigate severity of laminitis.

16 Claims, No Drawings

MAST CELL STABILIZERS TO PREVENT OR TREAT LAMINITIS

RELATED APPLICATIONS

This application claims priority to U.S. application Ser. No. 12/387,166 filed Apr. 29, 2009 and entitled "Nedocromil Sodium used to Inhibit Laminitis", which claims priority to U.S. application Ser. No. 11/047,068 filed Jan. 31, 2005 and entitled "Mast Cell Stabilizers Used to Inhibit Laminitis", which claims priority to U.S. Provisional Application Ser. No. 60/598,186 filed Aug. 2, 2004 and entitled "Nedocromil Sodium used to Inhibit Laminitis and the Stress Response in Horses", each of which is hereby incorporated by reference in its entirety.

TECHNICAL FIELD

The present disclosure relates to treating or preventing laminitis, and in particular, using mast cell stabilizers to treat or prevent laminitis.

BACKGROUND

The statements in this section merely provide background information related to the present disclosure and may not constitute prior art.

Laminitis is a complex disease process in horses which includes inflammation of the sensitive lamina along the dorsal aspect of the foot, and results in detachment of the bone (distal phalanx) from the hoof wall with subsequent downward rotation or distal displacement of the bone (founder). Affected animals are often in severe pain, prone to recurrent episodes, and in many cases must be destroyed due to the permanent damage that occurs within the hoof. Numerous predisposing factors may contribute to the development of laminitis, but the pathogenesis remains undetermined.

Several theories have been proposed for the development of laminitis including the "vascular" hypothesis and the "toxic/metabolic" hypothesis. The vascular hypothesis suggests the primary problem exists in dysfunction of the digital vasculature resulting in digital tissue ischemia—any subsequent problem including metabolic dysplasia, inflammatory processes, and structural failure is due to the initial ischemic event. The toxic/metabolic hypothesis proposes "trigger factors" or toxins which directly damage the epidermal cells or basement membrane of the laminae resulting in tissue destruction while subsequent vascular, structural, and inflammatory changes are considered secondary to the damage caused by the toxins. The primary difference between the two theories is that the vascular theory involves reduced digital blood flow (ischemia) and the toxic/metabolic theory involves increased digital blood flow.

In general, laminitis is a local manifestation of a systemic disease. Affected horses, for example, often present with a gastrointestinal system event which contributes to the disease processes within the feet. A common scenario involves an animal that eats too much grain or lush pasture or develops a gastrointestinal tract infection. Gut fermentation is altered and the intestinal mucosal barrier is damaged resulting in absorption of toxins to the peripheral circulation. The toxins are theorized, as discussed above, to directly damage the laminae or to alter blood flow to the digit resulting in laminar ischemia.

Additional laminitis predisposing factors include grain overload, colitis, small intestinal strangulation/obstruction, proximal enteritis, metritis, pleuropneumonia, and any other condition involving septicemia or toxemia. Often, however, the true cause is unknown.

Bovine lactic acidosis results from diets high in ruminally available carbohydrates or forage too low in effective fiber, and is associated with large increases of lactic acid in the rumen. Clinical manifestations range from loss of appetite to death while laminitis is implicated physiologically. The challenge to the dairy industry is more often subclinical acidosis rather than acute acidosis. Subclinical acidosis is characterized by a decrease in pH with only very little accumulation of lactic acid in the rumen. Repeated episodes of pH<5.5 for given periods ultimately predispose cattle to low grade, subclinical acidosis, the symptoms of which include erratic appetite, weight loss, diarrhea, and lameness as a result of laminitis.

Laminitis is also a problem for mules, donkeys, sheep, pigs, goats, camels, and other hoofed animals.

Conventional treatment of laminitis varies depending on the perceived underlying cause. Initial treatment can involve intravenous fluid therapy, systemic antimicrobials, intravenous dimethyl sulfoxide, anti-inflammatory drugs, and administration of mineral oil with a nasogastric tube. Non-steroidal anti-inflammatory drugs are used to decrease inflammation within the foot, and other drugs used to improve blood flow to the laminae of the affected foot. Unfortunately, standard treatments fail to consistently provide relief and prevent damage.

Regardless of the cause, laminitis results in damage and irreversible changes to the hoof, not to mention the extensive pain for the animal involved. The owner's cost of treatment and the expense involved in the loss of use of the animal are further challenges that need to be addressed.

The present invention is directed toward overcoming one or more of the problems discussed above.

British Patent Specification No 2,022,078 mentions a large number of pyranoquinolinone derivatives purportedly useful as prophylactic inhalation anti-asthmatics when administered as unit dosages of from 0.01 to 10 mg in admixture with coarse lactose. This patent specification also mentions the disodium salt of 9-ethyl-6,9-dihydro-4,6-dioxo-10-propyl-4H-pyrano[3,2-g]-quinoline-2,8-dicarboxylic acid, which salt is commonly known as nedocromil sodium or TILADE™.

Against this backdrop the present disclosure is provided.

SUMMARY

Provided herein are innovations with respect to treating, preventing, and mitigating laminitis.

In one embodiment, a method is provided for the treatment of laminitis. The method comprises administering a mast cell stabilizer to a subject in need thereof.

In another embodiment, a method is provided for the treatment of laminitis. The method comprises inhibiting mast cell degranulation in a subject in need thereof.

In still another embodiment, a method is provided for preventing laminitis. The method comprises identifying a subject at risk for laminitis and administering a mast cell stabilizer to the subject.

In yet another embodiment, a method is provided for treating chronic laminitis. The method comprises administering a mast cell stabilizer to a subject in need thereof.

In another embodiment, a method is provided for mitigating the severity of laminitis. The method comprises administering a mast cell stabilizer to a subject in need thereof.

DETAILED DESCRIPTION

These and other feature as well as advantages which characterize the invention will be apparent from a reading of the following detailed description and a review of the appended claims.

The following description is merely exemplary in nature and is in no way intended to limit the present disclosure, application, or uses.

Provided herein are methods and compositions for treating, preventing, or mitigating laminitis, including treating, preventing, or mitigating acute laminitis, subclinical laminitis, and chronic laminitis. The compositions comprise, consist of, or consist essentially of one or more mast cell stabilizers alone or in combination with a further medicament.

Laminitis

Laminitis is an aseptic inflammation of the dermal layers inside the foot, the scientific name of which is pododermatitis aseptic diffusa. The connective tissue within the foot attaches the foot bone to the hoof wall; when the connective tissue becomes inflamed, it dies and the bone detaches from the hoof wall. As described below, laminitis also affects the whole animal and occurs in acute, subclinical, and chronic forms.

Though the discussion throughout is generally directed to cows and horses, methods and compositions are equally applicable to any hoofed animal afflicted by laminitis. Illustratively, a subject described herein can include, but is not limited to, a horse, pig, cow, sheep, goat, mule, donkey, buffalo, and camel. Further, a subject can also include any hoofed animal maintained in a zoo, for example, a zebra, giraffe, elephant, etc.

Stressors and the Developmental Phase

In general, laminitis is initiated by a stressor—any event or substance that upsets the homeostasis of the animal. Stressors can be external to the animal or internal to the animal. Either way, the stressor is a perceived threat to which the animal's body generates a response. Stressors include substances that the animal is exposed to in quantities larger than the animal is used to, and substances foreign to the animal. Illustratively, substance stressors cause pasture founder, grain founder, carbohydrate overload, and colic. Stressors also include mechanical insults, e.g. standing on a hard surface for an extended period of time, trailering for long periods, improper shoeing, ground concussion, snake bites, blow to the head, electric shock, etc.

Exposure of an animal to the stressor initiates a developmental phase of laminitis. The developmental phase occurs over a period of up to 72 hours due to a delayed hypersensitivity reaction to the stress response. While not wishing to be bound by theory, it is believed that the stressor signals the animal's central nervous system through the nervous or humoral pathways. The hypothalamus activates the autonomic nervous system which in turn generates the "fight or flight" response, overall body arousal, and end-organ response. The adrenal gland releases catecholamines, including epinephrine, which induces hyperglycemia resulting in increased blood glucose levels. Circulating levels of glycerol and free fatty acid are also increased.

Epinephrine and norepinephrine cause blood vessels in the skin and abdominal viscera to constrict while blood vessels supplying the heart and skeletal muscles dilate. Thus, blood flow shifts from non-vital areas of the body to areas important for short term survival.

Cortisol is essential for maintaining a proper balance of blood sugar—a drop in blood sugar levels causes the adrenal gland to make cortisol. Upon exposure to a stressor, cortisol is released into the blood to minimize damage caused by elevated blood sugar and to induce insulin resistance. Cortisol is also an anti-inflammatory and helps reduce swelling in tissues.

In response to a stressor, blood is directed away from the digestive system resulting in decreased oxygen delivered to the mucosal cells that line the digestive tract. The lack of oxygen results in higher levels of lactic acid fermentation in the gut. A build up of high levels of lactic acid causes activation of the mast cells located in the digestive tract tissues.

Compositions and methods described herein are useful in addressing laminitis in this stage. For example, if a care giver, i.e., owner, veterinarian, caretaker, veterinarian nurse/technician, etc., identifies an animal that may be at risk of laminitis as the animal exhibits a change in behavior conducive with laminitis, because the animal exhibits physical signs of laminitis, or because the animal was exposed to a stressor with the potential to initiate laminitis, a mast cell stabilizer can be administered to the animal to prevent, treat, or mitigate the severity of laminitis.

Acute Phase

The hormones epinephrine, norepinephrine, and cortisol are secreted in response to the stressor to the point of exhaustion. After exhaustion, hormone output is diminished and thus their effectiveness diminished. In response, mast cells release vasodilators in an attempt to establish normal blood flow back to the muscles and extremities.

Mast Cells

Mast cells reside in several types of tissues and contain histamine and heparin rich granules. Mast cells also contain metalloproteinase-2 and -9, as well as dopamine and serotonin. Believed to have originated from bone marrow precursors expressing the CD34 molecule, a circulating mast cell is immature and does not mature until settling into a tissue site. There are two types of mast cells: those resident in connective tissue and those resident in mucosal tissue. Mucosal mast cell activity appears to be dependent upon T-cells.

Mast cells are involved in the inflammatory process, rapidly releasing granules into the interstitium upon activation. Mast cell degranulation can be stimulated by direct injury (either physical or chemical), by crosslinking of immunoglobulin E receptors, or by activated complement proteins.

Histamines and Matrix Metalloproteinases

Histamine is a proinflammatory mediator, selectively located in the granules of mast cells and basophil granulocytes and released upon degranulation. Mast cells and basophil granulocytes produce histamine in large quantities which are then stored in intracellular vesicles. Histamine regulates physiological function in the gut and acts as a neurotransmitter. Histamine also increases the permeability of capillaries to white blood cells and other proteins, causes contraction of smooth muscle, and dilation of blood vessels.

Connective tissue mast cells can be located in the hoof laminae and release histamine to open up constricted vessels such that blood flow to the area (and particularly the capillary bed) increases. In laminitis, histamine is typically more active in the initial phase of acute inflammation.

Matrix metalloproteinases (MMPs) are also released along with histamine after exposure to a stressor. Excess MMP released from the mast cell may target the laminae of the laminar corium that bonds the bone to the foot. As a result, the epidermal cells detach from the basement membrane of the laminae contributing to the damage to the hoof.

Delayed-type Hypersensitivity

The delayed allergic reaction in laminitis is a cell mediated immune response which enables the body to defend against antigens that cannot be effectively mitigated by antibodies. A cell mediated response is triggered when T-cells recognize an antigen; in laminitis, the antigen can be excess histamine. Depending on the size, breed, and resistance level of the animal, the delayed hypersensitivity reaction may develop hours or days after histamine has entered the tissue. Even after sensitivity has developed, symptoms may not be visible for another 24 to 72 hours. This is referred to as the acute inflammation phase of laminitis.

Acute inflammation is observed in connective tissues where excess histamine causes blood vessels to dilate and become permeable to white blood cells and plasma. Local swelling, redness, heat, and pain are characteristic of leakage of the white blood cells and plasma into the laminar corium. Even at this point laminitis can be difficult to recognize—the animal demonstrates some discomfort noticeable in the shifting of its weight and eating and other related behavioral changes. Compositions and methods described herein are useful at this stage in treating the acute inflammation and decreasing potential damage.

As the acute inflammation phase escalates, the vascular permeability of the inflamed area increases. Histamine causes dilation of the arteries, precapillary sphincters open, and the capillaries swell and expand. Increased blood flow or hyperemia is responsible for the red coloration of the inflamed tissue. The increased vascular permeability allows plasma protein to leak through the vessel wall (exudation) decreasing the osmotic pressure effect of the proteins. Exudation occurs initially in the veins and later in the capillaries as well.

Compositions and methods described herein are also useful in the acute phase of laminitis. For example, a mast cell stabilizer can be administered to a subject in the acute phase to treat laminitis, to alleviate the associated symptoms, and/or to mitigate the severity of the disorder.

Resolution

Resolution occurs when the inflamed tissue returns to normal following acute inflammation and usually takes place when tissue damage is slight or reversible. When acute inflammation involves an epithelial surface, the covering is destroyed and an ulcer is formed. The ulcer is covered by dead tissue and exudates, or slough, which detaches and allows the damaged hoof to regenerate. In severe cases of laminitis, the whole hoof will slough and an entire hoof will be regenerated.

Compositions and methods described herein are also useful in the resolution phase of laminitis. For example, a mast cell stabilizer can be administered to a subject in the resolution phase to treat laminitis, to alleviate the associated symptoms, and/or to mitigate the severity of the disorder.

Founder Phase

Founder is a potential consequence of severe acute laminitis or chronic laminitis. Physiologically, founder is the rotation and sinking of the $3^{rd}$ phalanx (and sometimes the $1^{st}$ and $2^{nd}$ phalanx) as a result of separation of the dermal and epidermal laminae. Not all animals that experience laminitis will founder, though any animal that founders will have first experienced laminitis. Relative to cattle, sheep, goats, and some other hoofed animals, founder in horses can be substantially worse. In some cases, the $3^{rd}$ phalanx may rotate far enough to penetrate the bottom of the horse's hoof near the frog. Sinking is rare and more severe and involves the settling of the $3^{rd}$ phalanx as well as the $1^{st}$ and $2^{nd}$ phalanx.

Founder can occur in one foot, two feet, three feet, or four feet. Founder can occur equally in the back feet as in the front feet.

Compositions and methods described herein are also useful in the founder phase of laminitis. For example, a mast cell stabilizer can be administered to a subject in the founder phase to treat the underlying laminitis, to alleviate the associated symptoms, and/or to mitigate the severity of the founder.

Chronic Inflammation

In circumstances where the stressor is not removed, resolution of laminitis does not occur, and the animal will suffer from repeated episodes of laminitis, i.e. chronic laminitis. In such cases, destruction and inflammation occur alongside attempts to heal.

Pathologically, chronic inflammation is a mixture of the effects of tissue damage, inflammation, demolition, and healing. Excess histamine continues to be released into the blood stream and the delayed hypersensitivity reaction persists.

Compositions and methods described herein are also useful in the chronic phase of laminitis. For example, a mast cell stabilizer can be administered to a subject in the chronic phase to stop the laminitic cycle, to treat laminitis, to alleviate the associated symptoms, and/or to mitigate the severity of each recurring episode.

Compositions

The compositions herein can be used for mitigating, preventing, and treating laminitis in hoofed animals.

In some embodiments, the compositions herein are used to treat laminitis.

In other embodiments, the compositions herein are used to mitigate the severity of laminitis.

In still other embodiments, the compositions herein are used to prevent laminitis.

Thus, in some cases, a composition herein is administered to an animal to treat, mitigate the severity of, or prevent laminitis and in particular, to treat, mitigate the severity of, or prevent acute laminitis, subclinical laminitis, and/or chronic laminitis.

Mast Cell Stabilizers

Mast cell stabilizers are not antihistamines and are surprisingly and unexpectedly more effective than antihistamines in the treatment of laminitis. Mast cell stabilizers described herein inhibit mast cell degranulation and subsequent release of histamine and metalloproteinases, while antihistamines block the action of histamine on a target tissue.

While not wanting to be bound by theory, it is believed that the superiority of mast cell stabilizers over antihistamines can be attributed to the ability of mast cell stabilizers to prevent localized and/or systemic release of histamine and other mediators. Administration of a mast cell stabilizer to treat laminitis generates a consistent, uniform effect by acting upstream of histamine release.

Mast cell stabilizers do more than prevent histamine release from mast cells: mast cell stabilizers inhibit activation of several other types of cells, including eosinophils, neutrophils, monocytes, macrophages, and platelets, and inhibit the release of additional mediators such as leukotriene C4, prostaglandin D2, and various other cytokines.

Conversely, antihistamines block the action of histamine in a target tissue but fail act directly on the release of histamine or to mitigate activity of other mediators. Instead, antihistamines act directly on histamine released and thus can be overwhelmed by the level of histamine in the blood. When histamine levels are high, it is difficult to administer sufficient amounts of antihistamine to moderate the effects of histamine without antihistamine induced side effects. Unlike mast cell stabilizers, antihistamines are subject to local concentration of histamine at any given release point and thus the antihistamine can be underrepresented in some areas of the body or overrepresented in other. Mast cell stabilizers administered at any given concentration will prevent degranulation of mast cells regardless of the location in the body.

Exemplary mast cell stabilizers include cromone medications typically used to treat allergic disorders such as asthma, hay fever, allergic conjunctivitis. In general, these compounds act by blocking calcium channels essential for mast cell degranulation which stabilizes the cell to prevent release of histamine. Mast cell stabilizers include, but are not limited to nedocromil sodium, cromolyn sodium, pemirolast, lodoxamise trometamol, odoxamide, and sodium cromoglycate, lodoxamide, salbutamal, ketofin, terfenadine, and cetirizine. The structures of nedocromil and cromolyn are shown in Table 1.

TABLE 1

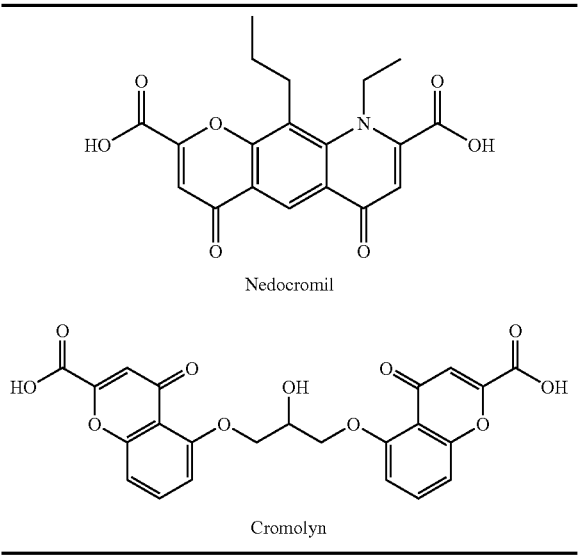

Nedocromil

Cromolyn

Mast cell stabilizers herein can be used to treat, mitigate the severity of, or prevent laminitis and in particular, to treat, mitigate the severity of, or prevent acute laminitis, subclinical laminitis, and/or chronic laminitis. In some embodiments, the mast cell stabilizer is a combination of two or more mast cell stabilizers described herein.

Mast Cell Stabilizers in Combination with Other Medicaments

Mast cell stabilizers can be used in combination with other medications used to treat the underlying cause of laminitis or symptoms associated with laminitis. These medications can be administered in the same formulation or in separate formulations, by the same route or by different routes, and at the same time or at different times.

Typical medications useful in combination with mast cell stabilizers include, for example, antihistamines, antiinflammatories, analgesics, etc. Exemplary antihistamines include benadryl, histadyl, trepelenneamine, pyrilaminic maleate, and chlortimeton maleate. Phenylbutazone and banamine are common pain relievers used in livestock. Other medications co-administered with mast cell stabilizers include cortisone, acetaminophen, buprenorphine, diclofenac, etodolac, fentanyl, etc.

When administered in combination with mast cell stabilizers, antihistamines can be used to inhibit activity of any secondary histamine released regardless of the presence of a mast cell stabilizer.

It is also contemplated herein that the mast cell stabilizers can be administered with stem cells. For example, as the animal is receiving the mast cell stabilizer intravenously, the caregiver can administer stem cells to the affected site.

Formulations

The compositions herein can be formulated with one or more carriers or excipients for delivery to a hoofed animal. Such carriers can be, for example, pharmaceutical carriers and veterinary carriers.

Typically such formulations will include one or more acceptable carriers, excipients, or diluents. Pharmaceutically acceptable carriers for therapeutic use are well known in the pharmaceutical art, and are described, e.g., in Remington's Pharmaceutical Sciences, Gennaro, A R, ed., 20th edition, 2000: Williams and Wilkins Pa., USA. which is incorporated herein by reference for all purposes. Veterinary excipients and carriers are also known in the art.

A pharmaceutical formulation can also contain any kind of other compatible ingredients such as, for example, protective colloids, adhesives, thickening agents, thixotropic agents, penetrating agents, stabilizing agents, sequestering agents, fertilizers, anti-freeze agents, repellents, color additives, corrosion inhibitors, water-repelling agents, UV-stabilizers, pigments, dyes or polymers.

In some embodiments, the compositions herein may be formulated as a salt and be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preparation may be a lyophilized powder which is combined with buffer prior to use.

After pharmaceutically and physiologically acceptable compositions have been prepared, they can be placed in an appropriate container and labeled for treatment of laminitis.

While any suitable carrier known may be employed in a pharmaceutical formulation of this invention, the type of carrier will vary depending on the mode of administration and whether a sustained release is desired. Routes of delivery may include oral, intravenous injection, intramuscular injection, subcutaneous injection, inhaled, buccal, intranasal, subdermal, and transdermal routes.

For parenteral administration, such as subcutaneous injection or intravenous injection, the carrier can include, for example, any one or more of the following ingredients: adjuvant, water, saline, alcohol, fat, wax, or buffer.

For oral administration, a carrier can comprise carbohydrate or polypeptide fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl-cellulose; gums including arabic and tragacant; and polypeptides such as gelatin and collagen. If desired, disintegrating or solubilizing agents may be added, such as the cross-linked polyvinyl pyrrolidone, agar, alginic acid, or a salt thereof, such as sodium alginate. If desirable, the drug can be delivered in nanocapsules that would protect against enzymatic or chemical degradation. Such carriers enable the compositions herein to be formulated as tablets, pills, dragees, capsules, liquids, gels, syrups, slurries, suspensions, and the like, for ingestion by the animal. Pharmaceutical preparations for oral use can be obtained through combining active compounds with solid excipient. The resulting mixture can optionally be ground and processed.

Formulations for topical administration can use a carrier that is a solution, emulsion, and ointment or gel base. The base, for example, may comprise one or more of the following: petrolatum, lanolin, PEGs, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

Biodegradable microspheres (e.g. polylactic galactide) may also be employed as carriers for the pharmaceutical compositions of this invention. Suitable biodegradable microspheres are disclosed, for example, in U.S. Pat. Nos. 4,897,268 and 5,075,109, each incorporated by reference herein for all purposes.

Pharmaceutical compositions may also contain diluents such as buffers, antioxidants such as ascorbic acid, low molecular weight (less than about 10 residues) polypeptides, polypeptides, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. In some cases the compositions herein are lyophilized using appropriate excipient solutions (e.g., sucrose) as diluents.

The compositions herein can be administered in a therapeutically effective dose to treat, mitigate, or prevent laminitis. As used herein, the words "treat", "treating", and "treatment" refer to the care provided to improve the condition of a subject afflicted with laminitis. As used herein, the words "mitigate" and "mitigating" refer to lessening the extent of or seriousness of laminitis, for example, to lessen, reduce, and/or diminish the effects of or severity of laminitis. As used herein, the words "prevent" and "preventing" refer to stopping or avoiding the effects of laminitis in a subject.

Pharmaceutically acceptable formulations include compositions wherein the active ingredients (e.g., one or more mast cell stabilizers alone or in combination with one or more of the following: antihistamine, analgesics, and antiinflammatories) are contained in an effective dose to achieve the intended purpose. The determination of an effective amount or dosage is well within the capability of those skilled in the art. Typically, an effective dose of a mast cell stabilizer for systemic administration is between about 0.5 mg/kg body weight to about 10 mg/kg body weight, or between about 1 mg/kg body weight to about 7 mg/kg body weight, or between about 3 mg/kg body weight to about 5 mg/kg body weight per dose. For example, an effective dose of a mast cell stabilizer for intravenous administration is between about 0.5 mg/kg body weight to about 10 mg/kg body weight, or between about 1 mg/kg body weight to about 7 mg/kg body weight, or between about 3 mg/kg body weight to about 5 mg/kg body weight per dose. For topical administration, the compositions herein may be delivered at dosage up to about 99%, 95%, 90%, 80%, 70%, 60%, 50%, 40%, or 30% w/w of the composition.

As mentioned above, compositions herein may be co-formulated or co-administered with a second therapeutic agent. Examples of therapeutic agents include, but are not limited to, analgesics, antipyretic medicaments (fever reducers), antihistamines, anti-inflammatories, antimicrobial agents (e.g., antibiotics, antiviral agents, and antifungal agents), and combinations thereof.

A therapeutically effective dose refers to that amount of active ingredient which prevents or diminishes the effects of laminitis. The dosage varies depending upon the dosage form employed, sensitivity of the animal, and the route of administration. The care giver, in light of factors related to the animal requiring treatment, will determine the exact dosage. Dosage and administration are adjusted to provide sufficient levels of the active compound or to maintain the desired effect. Factors which can be taken into account include the severity of the disease state, general health, age, and weight of the animal. Compositions may be administered several times a day for 1 day to 1 week, once a day, twice a day, three times a day, every other day, every 3 to 4 days, every week, once every two weeks, once a month, etc, depending on half-life and clearance rate of the particular formulation and on the risk of or progression of the laminitis. In some embodiments, the animal receives one dose of a mast cell stabilizer. In other embodiments, the animal receives two or more total doses of a mast cell stabilizer. In some embodiments, the animal has chronic laminitis or is prone to laminitis and thus, the animal is administered a mast cell stabilizer on a regular basis over an extended period of time.

Normal dosage amounts vary from 0.1 mg/kg to 10 mg/kg body weight depending upon the route of administration. In some aspects, the mast cell stabilizer is administered into the digital artery of an affected leg. The dosing in this aspect, for example, would be ¼ of the total dose. Guidance as to particular dosages and methods of delivery is provided above, in the literature, and generally available to practitioners in the art.

For local administration or topical administration lower dosage may be required. For repeated administrations over several days or longer, depending on the condition, the treatment is sustained until laminitis is avoided or suppressed in severity. However, other dosage regimens may be useful. It is anticipated that different formulations will be effective for different treatment compounds, e.g. different mast cell stabilizers alone or in combination with anti-inflammatories, anti-histamines, and/or analgesics.

The mast cell stabilizer compositions may be administered in the form of a solid, liquid, gel, spray, or gas (aerosol). For example, for oral administration as a pharmaceutical formulation the composition can be delivered as a syrup, lozenger, pill, gel capsule, etc. For subdermal or subcutaneous delivery, it can be delivered in a liquid formulation. For topical administration, the pharmaceutical composition can be delivered as a gel, cream or patch. For delivery to the lungs, the composition can be in a liquid spray, spray of fine solid particles, or gas.

Thus, provided herein is a pharmaceutical formulation comprising, consisting of, or consisting essentially of a mast cell stabilizer and a pharmaceutical excipient.

Any of the excipients described herein or any other ones known in the art can be used according to the present invention.

The pharmaceutical composition is formulated so as to allow the active ingredient(s) contained therein to be bioavailable upon administration of the composition to an animal. Compositions that will be administered to the animal take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, compositions can contain, in addition to the compositions herein one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent can be included.

Injectable formulations of the compositions herein are preferably sterile. Means for achieving sterility are well known in the art.

For delivery to the dermis and/or epithelium, dermal patches and delivery systems utilizing active or passive transdermal delivery carriers can be prepared using well known methods and materials, including, for example, microporous membranes, silicon polymers and diffusion matrixes. Such materials and methods are described, for example, in: Remington's Pharmaceutical Sciences, supra.

The compositions (including formulations) herein can be administered systemically or locally to a hoofed animal by any means known in the art. For example, to an animal such as a horse, the compositions herein can be administered parenterally (which includes subcutaneously, intravenously, intramuscularly, intrasternally, intracavernously, intrathecally, and intraurethrally), intracranially, intraorbitally, intracapsularly, intraspinally, intracisternally, intrapulmonarily (via inhalation), orally, intravenously, intra-arterially, intramedullary, intrathecally, intraventricularly, transdermally, subcutaneously, intraperitoneally, intranasally, enterally, vaginally, sublingually, or rectally. In some embodiments, the composition/formulations herein are administered using insert(s), bead(s), timed-release formulation(s), patch(es) or fast-release formulation(s).

The compositions/formulations herein are administered in an effective dose. It will be evident to those skilled in the art that the number, frequency, and duration of administration will be dependent upon the response of the animal.

Kits

Provided herein are kits having components useful in preventing, treating, or mitigating severity of laminitis. Such kits can include, but are not limited to, one or more mast cell stabilizers, one or more additional medicaments, devices useful in administering the medicaments, instructions for using the kit components, etc.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

All references cited herein are incorporated by reference in their entirety and to the same extent as if each individual publication or patent application was specifically and individually indicated to be incorporated by reference.

EXAMPLES

The following examples are provided for illustrative purposes only and are not intended to limit the scope of the invention.

Example 1

Histological Evaluation of Treatment in an Acute Model of Ovine Laminitis

Laminitis can be induced in vivo through systemic acidosis. This study initiated laminitis in anesthetized sheep by inducing acidosis for the purpose of measuring the level of inflammation in the hoof vascular bed associated with initiation of laminitis.

Adult Suffolk sheep (at least 6 months old) weighing at least 60 kg were obtained for the study. Animals were housed and research procedures were performed according to the standards provided in the Guide for the Care and Use of Laboratory Animals, $7^{th}$ Edition, Revised 1996, National Academy Press, Washington, D.C. During acclimation, sheep were pasture-housed with access to feed, water, and shelter. Sheep were fed a standard diet of hay and alfalfa in addition to pasture feed. One day prior to surgery, each animal was transferred to an indoor facility with single animal runs. Each had an area greater than 24 square foot and had elevated floors. The runs had automatic watering devices and animals were fed in steel feeders. Animals were acclimated for a minimum of one day prior to surgery. Sheep were fasted approximately 16 hours overnight on the day prior to surgery.

Temperatures were maintained between 18° C. and 29° C., humidity maintained between 20% and 70%, and light set to a cycle of 12 hours on/12 hours off.

Two sheep served as terminal controls after prolonged infusion of lactic acid and the mast cell activator 48/80. Systemic blood pH was lowered to approximately 5.5, the animals euthanized, and the hooves observed histopathologically.

Two additional sheep received infusions of lactic acid and histamine as did the control sheep, but further received a controlled bolus dose of the mast cell stabilizer Nedocromil sodium.

The fifth sheep was used as an untreated control and the sixth sheep as a back-up patient in the event that any one of the first five experienced complications under anesthesia.

Intra-operative acidosis was monitored using an iSTAT® monitor and measurements were taken at 15 minute intervals.

Nedocromil sodium was prepared at a concentration of 150 mg/mL in sterile saline. Compound 48/80 was prepared at a concentration of 1 mg/mL in sterile saline. Lactic acid was formulated at 750 mg/mL in sterile saline. Concentrates were stored at 2-8° C. prior to use.

Sheep were anesthetized at the time of surgery and maintained under isoflurane with mechanical ventilation for the duration of the procedure. External jugular veins were catheterized—one for infusion of test solutions, the other for intra-operative blood sampling.

TABLE 2

| Group No. | Number of Animals | Treatment | Rate |
| --- | --- | --- | --- |
| 0 | 1 | Saline | About 60 mL/hour |
| 1 | 2 | Lactic acid infusion + Compound 48/80 (1 mg/kg) | To effect |
| 2 | 2 | Nedocromil sodium (42 mg/kg) + Lactic acid infusion + Compound 48/80 (1 mg/kg) | To effect |

To induce lactic acidosis, racemic lactic acid (65% L and 35% D) was infused at a rate of 1.5 g/minute. Blood samples were obtained immediately following infusion to measure histamine concentration and at 15 minute intervals to monitor the levels of induced acidosis. For sheep receiving Nedocromil sodium, the same procedures and time frames were used except immediately before and after lactic acidosis was established, a single dose of Nedocromil sodium was administered.

Following a two hour refractory period subsequent to infusion, animals were euthanized while still under anesthesia and hooves harvested for histological analysis.

Tissue sections were obtained from the hooves after decalcification and blocking. The sections were stained with hematoxylin and eosin, then examined microscopically.

TABLE 3

| Animal Number | Hoof Number | Group Number | Findings |
|---|---|---|---|
| 1 | 1A | 0 | No significant findings |
| 1 | 1B | 0 | No significant findings |
| 2 | 1A | 0 | No significant findings |
| 2 | 2A | 0 | No significant findings |
| 3 | Right | 1 | Inflammation, acute, moderate in the connective tissue of the lamina layer. The polymorphonuclear cells were in the connective tissue between keratinized lamina cells. The inflammation appeared to be near the junction of hoof and skin. |
| 3 | Left | 1 | No significant findings |
| 4 | Right | 1 | No significant findings |
| 4 | Left | 1 | Inflammation, acute, moderate in the inner portion of the lamina and junction of underlying connective tissue. Section contained mostly sole and little wall. |
| 5 | 1 Right Toe | 2 | No significant findings |
| 5 | 1 Left Toe | 2 | No significant findings |
| 5 | 2 Right Toe | 2 | No significant findings |
| 5 | 2 Left Toe | 2 | No significant findings |

Twelve sheep toes (hooves) were submitted for histological evaluation. Two hooves had acute inflammation present—two of the lactic acid positive control specimens. The inflammation consisted of a moderate infiltrate of polymorphonuclear cells in the lamina between the wall of the hoof and underlying bone. In one section the inflammation was in the lamina near the junction of hoof and skin, and in the other, the inflammation was further distal and in the inner lamina extending into the underlying connective tissue. No inflammation was observed in the negative control specimens or in any specimens from Nedocromil sodium treated animals.

This example demonstrates treatment with the mast cell stabilizer, Nedocromil sodium, effectively reduced short-term inflammation induced by metabolic acidosis in combination with compound 48/80.

Example 2

Evaluation of Horses Presenting with Laminitis or Colic Relative to Normal

The objective of this study was to determine concentrations of adrenocorticotrophic hormone (ACTH), cortisol, insulin, thyroid hormone, glucose, and histamine within the peripheral blood of healthy horses, horses with gastrointestinal diseases known to predispose to laminitis, and horses with clinical laminitis. Clinical laboratory kits were used to assay the desired markers from peripheral blood samples.

Adult horses two years of age and older were presented to the Veterinary Teaching Hospital by owner clients. Twelve horses having colic or colitis, 14 horses having laminitis, and 12 normal horses participated in the study.

Peripheral blood was drawn from the left jugular vein of each horse. The serum and plasma was separated, placed in plastic vials, and frozen at −70° C. until analysis. ACTH, thyroid hormone, cortisol, and histamine levels were determined using commercially available clinical kits.

TABLE 4

| | Normal Horses | | | | |
|---|---|---|---|---|---|
| sample # | sample type | T4 (μg/dl) | eACTH (pg/mL) | Cortisol (μg/dl) | Histamine (pg/mL) |
| 5 | ser, plasma-eACTH, plasma-hist. | 2.5 | 21.2 | 2 | 5.28 |
| 13 | ser, plasma-eACTH, plasma-hist. | 1.5 | <10.0 | 4.8 | 4.97 |
| 14 | ser, plasma-eACTH, plasma-hist. | 2.4 | 13.5 | 5 | 5.55 |
| 15 | ser, plasma-eACTH, plasma-hist. | 1.8 | 37.5 | 6.3 | 7.44 |
| 16 | ser, plasma-eACTH, plasma-hist. | 1.9 | 14.8 | 4.1 | 6.82 |
| 18 | ser, plasma-eACTH, plasma-hist. | 1.4 | <10.0 | 3.9 | 7.03 |
| 19 | ser, plasma-eACTH, plasma-hist. | 3.4 | 15.7 | 4.9 | 6.18 |
| 25 | ser, plasma-eACTH, plasma-hist. | 1.1 | 12 | 7.6 | 4.99 |
| 32 | ser, plasma-eACTH, plasma-hist. | 2.4 | 34.2 | 8.3 | 11.44 |
| 33 | ser, plasma-eACTH, plasma-hist. | <1.0 | <10.0 | 2.2 | 6.7 |
| 40 | ser, plasma-eACTH, plasma-hist. | 1.8 | 11.5 | 1.4 | 7.64 |
| 41 | ser, plasma-eACTH, plasma-hist. | 2.4 | 15.5 | 3.5 | 7.65 |
| | Mean | 2.05 | 19.54 | 4.5 | 6.80 |
| | St. Dev | 0.65 | 9.69 | 2.14 | 1.77 |
| | Median | 1.9 | 15.5 | 4.45 | 6.76 |

TABLE 5

Colitis/Colic Horses

| sample # | sample type | T4 (μg/dl) | eACTH (pg/mL) | Cortisol (μg/dl) | Histamine (pg/mL) |
|---|---|---|---|---|---|
| 9 | ser, plasma-eACTH, plasma-hist. | <1.0 | 32.7 | 9.5 | 4.64 |
| 10 | ser, plasma-eACTH, plasma-hist. | <1.0 | 37.3 | 5.3 | 10.74 |
| 20 | ser, plasma-eACTH, plasma-hist. | <1.0 | 13.2 | 8.3 | 4.15 |
| 21 | ser, plasma-eACTH, plasma-hist. | <1.0 | 22.7 | 6.3 | 6.57 |
| 22* | ser | <1.0 | | 12.9 | |
| 23 | ser, plasma-eACTH, plasma-hist. | <1.0 | 143 | 18.9 | 8.02 |
| 27 | ser, plasma-eACTH, plasma-hist. | <1.0 | 18.1 | 11.3 | 7.2 |
| 28 | ser, plasma-eACTH, plasma-hist. | <1.0 | <10.0 | 6.1 | |
| 29 | ser, plasma-eACTH, plasma-hist. | 1.1 | 16.5 | 7.5 | 7.12 |
| 30 | ser, plasma-eACTH, plasma-hist. | <1.0 | 43.3 | 7.8 | 5.3 |
| 34 | ser, plasma-eACTH, plasma-hist. | <1.0 | 124 | 15.3 | 8.45 |
| 38 | ser, plasma-eACTH, plasma-hist. | 1.1 | 46.6 | 8.1 | 9.91 |
| 43 | ser, plasma-eACTH, plasma-hist. | <1.0 | 390 | 13.6 | 5.31 |
| | Mean | 1.1 | 80.67 | 10.07 | 7.04 |
| | St. Dev | 0 | 111.41 | 4.07 | 2.13 |
| | Median | 1.1 | 37.3 | 8.3 | 7.12 |

*Plasma sat past 30 min. mark

TABLE 6

Laminitis Horses

| sample # | sample type | T4 (μg/dl) | eACTH (pg/mL) | Cortisol (μg/dl) | Histamine (pg/mL) |
|---|---|---|---|---|---|
| 1 | ser, plasma-eACTH, plasma-hist. | 2.6 | 14.4 | 5.1 | 11.2 |
| 2 | plasma-hist. | 1.4 | 13.7 | 8.3 | 7.88 |
| 3 | ser, plasma-eACTH, plasma-hist. | 1.6 | 16.9 | 3.7 | 8.08 |
| 4 | ser, plasma-eACTH, plasma-hist. | 1 | 16.5 | 4.3 | 7.4 |
| 11 | ser, plasma-eACTH, plasma-hist. | <1.0 | 15.5 | 3.6 | 6.33 |
| 12 | ser, plasma-eACTH, plasma-hist. | <1.0 | 6.1 | 23.2 | 8.91 |
| 24 | ser, plasma-eACTH, plasma-hist. | 1.8 | 27.1 | 8.7 | 7.04 |
| 26 | ser, plasma-eACTH, plasma-hist. | 2 | 22.2 | 11.5 | 6.98 |
| 31 | ser, plasma-eACTH, plasma-hist. | 2 | 31.9 | 9.6 | 7.35 |
| 35 | ser, plasma-eACTH, plasma-hist. | 2 | 124 | 3 | 7.26 |
| 36 | ser, plasma-eACTH, plasma-hist. | 2.1 | 55.1 | 4.6 | 8.18 |
| 37 | ser, plasma-eACTH, plasma-hist. | 2.9 | 26.3 | 2.6 | 8.02 |
| 39 | ser, plasma-eACTH, plasma-hist. | <1.0 | 662 | 15.8 | 7.86 |
| 42 | ser, plasma-eACTH, plasma-hist. | <1.0 | 78.8 | 4 | 13.91 |
| 44 | ser, plasma-eACTH, plasma-hist. | 3.9 | 17.8 | 3.6 | 12.91 |
| | Mean | 2.12 | 75.22 | 7.44 | 8.62 |
| | St. Dev | 0.79 | 165.29 | 5.75 | 2.24 |
| | Median | 2 | 22.2 | 4.6 | 7.88 |

After standardizing the data to the control, NPAR1WAY procedure was performed using Wilcoxon Scores (rank sums) for each variable and classified by group. Summaries of this analysis are provided in Tables 7-10.

TABLE 7

Wilcoxon Scores (Rank Sums) for Variable T4
Classified by Variable Group

| Group | N | Sum of Scores | Expected Under H0 | Std. Dev. Under H0 | Mean Score |
|---|---|---|---|---|---|
| Colic | 12 | 109 | 234 | 31.01 | 9.08 |
| Laminitis | 14 | 326 | 273 | 32.18 | 23.29 |
| Normal | 12 | 306 | 234 | 31.01 | 25.50 |

TABLE 8

Wilcoxon Scores (Rank Sums) for Variable eACTH
Classified by Variable Group

| Group | N | Sum of Scores | Expected Under H0 | Std. Dev. Under H0 | Mean Score |
|---|---|---|---|---|---|
| Colic | 11 | 257.50 | 209.0 | 30.07 | 23.41 |
| Laminitis | 14 | 266.0 | 266.0 | 31.91 | 21.68 |
| Normal | 12 | 228.0 | 228.0 | 30.80 | 11.83 |

TABLE 9

Wilcoxon Scores (Rank Sums) for Variable Cortisol
Classified by Variable Group

| Group | N | Sum of Scores | Expected Under H0 | Std. Dev. Under H0 | Mean Score |
|---|---|---|---|---|---|
| Colic | 12 | 345.50 | 234.0 | 31.83 | 28.79 |
| Laminitis | 14 | 237.00 | 273.0 | 33.03 | 16.93 |
| Normal | 12 | 158.50 | 234.0 | 31.83 | 13.21 |

TABLE 10

Wilcoxon Scores (Rank Sums) for Variable Histamine Classified by Variable Group

| Group | N | Sum of Scores | Expected Under H0 | Std. Dev. Under H0 | Mean Score |
|---|---|---|---|---|---|
| Colic | 10 | 169.50 | 185.0 | 28.31 | 16.95 |
| Laminitis | 14 | 332.50 | 259.0 | 30.81 | 23.75 |
| Normal | 12 | 164.00 | 222.0 | 29.80 | 13.67 |

The standardized data shows that histamine has an active role in laminitis as histamine levels in horses with laminitis are substantially higher than histamine levels in normal or colic horses.

Example 3

Use of Nedocromil Sodium to Prevent Bovine Laminitis

Subclincal laminitis, or subacute laminitis, in dairy cattle manifests primarily as sole hemorrhage, sole abscess, sole ulcer, and white line disease and is associated with subacute ruminal acidosis. High producing dairy cattle are commonly affected.

To test the effectiveness of nedocromil sodium to prevent laminitis in cattle, 4 Holstein calves weighing between 325 and 350 pounds were selected for the study and treated as shown in Table 11.

TABLE 11

| Animal ID | Body Weight, Pounds | Treatment |
|---|---|---|
| 1 | 325 | Administration of nedocromil sodium prior to carbohydrate mixture |
| 2 | 345 | Administration of nedocromil sodium prior to carbohydrate mixture |
| 3 | 325 | Administration of carbohydrate mixture |
| 4 | 350 | Administration of carbohydrate mixture |

Starting with day one through day four, and continuing day six through day seven, calves 1 and 2 received Nedocromil sodium pretreatment (1.5 grams infused through the jugular vein) while calves 3 and 4 received no treatment. On each of days one through four and days six through seven, blood samples were obtained from all four calves. No treatments were administered on days eight through ten. On day eleven, calves 1 and 2 were administered 2 grams of Nedocromil sodium. Shortly thereafter, 3.5 pounds of corn starch and 1.5 pounds of sugar mixed in water along with $6 \times 10^{11}$ lactic acid producing and histamine producing organisms were administered to all four calves by releasing the mixture into the rumen of each animal. The process of administering the carbohydrate plus lactic acid producing and histamine producing organisms is known to induce acidosis in cattle.

The calves' behavior was observed, blood samples taken, and temperatures measured over the next 72 hours.

Calf number 3 exhibited signs of lactic acidosis and examination of the calf's hoofs showed lesions associated with laminitis. Lactic acidosis could not be induced in calf number 4 even though the calf was not treated with nedocromil sodium—it is known in the field that some animals are naturally buffered against lactic acidosis.

Calves 1 and 2 were protected from lactic acidosis by the nedocromil sodium demonstrating the effectiveness of the compound as a preventative agent. Further, the study demonstrated lack of toxicity and/or side effects from the nedocromil sodium treatment.

Example 4

$Ca^{2+}$ Ionophore-Induced Histamine Release from *Rattus norvegicus* Basophilic Leukemia Cells The objective of this study was to determine if $Ca^{2+}$ ionophore stimulated the release of histamine and to determine whether treatment with nedocromil sodium changed the levels of histamine.

The immortal cell culture line of *Rattus norvegicus* basophilic leukemia cells was subcultured and incubated at 37° C. overnight. The following day, the supernatant was aspirated and histamine release induced by addition of various concentrations of $Ca^{2+}$ ionophore in Tyrode's buffer (supplemented with 10 mM Hepes, 1 g/L $NaHCO_3$, and 0.1% bovine serum albumin) for 30 minutes at 37° C. After incubation, 50 μL of the supernatant was removed from the cells and stored at −80° C. or derivatized for GC-MS analysis.

The supernatant was mixed with 135 μl of an acetone reaction solution (ethanol, triethylamine, and 9-methylanthracene) in a 0.5 ml microtube. After mixing for 10 seconds, 55 μl of a chloroform derivatization solution containing 100 μl ethylchloroformate was added and mixed for an additional 10 seconds. Then, 350 μL purified water was added and the two phases allowed to separate for 60 seconds. The organic phase was aspirated and placed into a 2 mL autosampler amber vial with glass inserts and dried with anhydrous sodium sulfate before being capped with GC vial snap caps.

The organic phase samples were dried and analyzed on an Agilent GC/MS 6890/5975C system with MS Chem Station software. Gas chromatography was carried out using a fused silica DB-WAX precolumn (0.2m×0.25 mm, $d_F$=0.25 μm), and a fused silica DB-WAX separation column (4m×0.25 mm, $d_F$=0.25 μm). Ultra high purity He was used as the carrier gas.

The GC parameters were set as follows: injection time was set to 5 μl using the splitless mode. After 120 seconds the split valve was opened with a 40 mL/minute split flow and front inlet temperature was held at 150° C. The oven temperature was ramped, starting at 60° C. for 2 minutes then increased at 50° C./minute to 160° C., then increased at 20° C./minute to 260° C. and held for 2.5 minutes. The MS detector was maintained at 300° C., with a solvent delay of 7 minutes, ion m/z 192 at 7.0-8.7 minutes, dwell time 100 ms, low-mass resolution; ion m/z 166, m/z 154 at 8.7-11.5 minutes, dwell time per ion 100 ms, low-mass resolution.

Several GC/MS standards with a range from 0.01-10 μg/ml of histamine, prepared from a histamine stock solution of 10-20 mg/mL in 0.1 M HCl, were derivatized in the same manner as described above, and a calibration curve created using 9-mathylanthracene internal standard solution as a retention time reference.

Based on the success of the $Ca^{2+}$ ionophore stimulated release of histamine, lactic acid at different concentrations was added to the cells to determine if lactic acid stimulated the release of histamine. Several doses of the compound, nedocromil sodium, were also tested. The data is shown in Table 12 and indicates that with increasing levels of nedocromil sodium, levels of histamine decreased. From this experiment it was concluded that nedocromil sodium is effective in inhibiting histamine release.

TABLE 12

| Treatment | Histamine Levels |
| --- | --- |
| Lactic acid | 16.286 |
| Lactic acid + 1 µl nedocromil sodium | 15.810 |
| Lactic acid + 2 µl nedocromil sodium | 14.470 |

The description of the present invention has been presented for purposes of illustration and description, but is not intended to be exhaustive or limiting of the invention to the form disclosed. The scope of the present invention is limited only by the scope of the claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

Various embodiments of the disclosure could also include permutations of the various elements recited in the claims as if each dependent claim was multiple dependent claim incorporating the limitations of each of the preceding dependent claims as well as the independent claims. Such permutations are expressly within the scope of this disclosure.

All references cited above are incorporated herein by reference in their entirety.

The words "comprise", "comprises", and "comprising" are to be interpreted inclusively rather than exclusively.

What is claimed is:

1. A method for the treatment of laminitis, the method comprising administering cromolyn sodium to a horse in need thereof, wherein the cromolyn sodium is administered through an intravenous injection in a dose of between about 0.5 and about 10 mg/kg of the horse's body weight and wherein the cromolyn sodium treats laminitis in the horse.

2. The method of claim 1, wherein the horse suffers from acute laminitis and has one or more affected sites and wherein the cromolyn sodium is administered directly to each of the one or more affected sites.

3. The method of claim 1, wherein the horse suffers from acute laminitis and wherein the cromolyn sodium is administered in a single dose.

4. The method of claim 1, the method further comprising administering another intravenous dose of cromolyn sodium to the horse within about 3 to 4 days after administering a first dose.

5. A method for the treatment of laminitis, the method comprising administering nedocromil sodium to a horse in need thereof, wherein the nedocromil sodium is administered through an intravenous injection in a dose of between about 0.5 and 10 mg/kg of the horse's body weight and wherein the nedocromil treats laminitis in the horse.

6. The method of claim 5, wherein the horse suffers from acute laminitis and has one or more affected sites and wherein the nedocromil sodium is administered directly to the each of the one or more affected sites.

7. The method of claim 5, wherein the horse suffers from acute laminitis and wherein the nedocromil sodium is administered in a single dose.

8. The method of claim 5, the method further comprising administering another intravenous dose of cromolyn sodium to the horse within about 3 to 4 days after administering a first dose.

9. The method of claim 1, wherein the dose is between about 1 and 7 mg/kg of the horse's body weight.

10. The method of claim 5, wherein the dose is between about 1 and 7 mg/kg of the horse's body weight.

11. The method of claim 1, where the horse suffers from chronic laminitis and wherein the cromolyn sodium is administered at least once a week.

12. The method of claim 5, where the horse suffers from chronic laminitis and wherein the nedocromil sodium is administered at least once a week.

13. The method of claim 1 wherein the dose is administered through an intravenous injection into the horse's one or more affected legs.

14. The method of claim 5 wherein the dose is administered through an intravenous injection into the horse's one or more affected legs.

15. The method of claim 13 wherein the intravenous injection is into a digital vein of the one or more affected legs.

16. The method of claim 14 wherein the intravenous injection is into a digital vein of the one or more affected legs.

* * * * *